(12) United States Patent
Matsui et al.

(10) Patent No.: US 7,616,805 B2
(45) Date of Patent: *Nov. 10, 2009

(54) PATTERN DEFECT INSPECTION METHOD AND APPARATUS

(75) Inventors: Shigeru Matsui, Hitachinaka (JP); Katsuya Suzuki, Hitachinaka (JP)

(73) Assignee: Hitachi High-Technologies Corporation, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/249,328

(22) Filed: Oct. 10, 2008

(65) Prior Publication Data

US 2009/0041335 A1 Feb. 12, 2009

Related U.S. Application Data

(63) Continuation of application No. 10/995,512, filed on Nov. 24, 2004, now Pat. No. 7,457,455.

(30) Foreign Application Priority Data

Nov. 28, 2003 (JP) ............................. 2003-398312

(51) Int. Cl.
*G06K 9/00* (2006.01)
(52) U.S. Cl. .................. 382/149; 250/559.45; 348/128; 348/129; 348/247; 382/199; 382/205; 716/4
(58) Field of Classification Search ............ 250/559.45; 348/128, 247, 129; 382/144, 149, 243, 141, 382/145, 199, 205; 716/1, 4, 19
See application file for complete search history.

(56) References Cited

U.S. PATENT DOCUMENTS 5,272,536 A * 12/1993 Sudo et al. .................. 348/243

5,574,800 A * 11/1996 Inoue et al. ................. 382/149

(Continued)

FOREIGN PATENT DOCUMENTS

JP 3-286383 12/1991

(Continued)

OTHER PUBLICATIONS

Japanese Office Action issued in Japanese Patent Application No. JP 2003-398312 dated Jan. 20, 2009.

*Primary Examiner*—Gregory M Desire
(74) *Attorney, Agent, or Firm*—McDermott Will & Emery LLP (57) ABSTRACT

The pattern defect inspection apparatus is operable to detect defects by comparing a detection image, which is obtained through scanning by an image sensor those patterns that have the identical shape and are continuously disposed on the object under tested at equal intervals in row and column directions, with a reference image obtained by scanning neighboring identical shape patterns in the row and column directions. This apparatus has a unit for generating an average reference image by statistical computation processing from the images of identical shape patterns lying next to the detection image including at least eight nearest chips on the up-and-down and right-and-left sides and at diagonal positions with the detection image being intermediately situated. The apparatus also includes a unit that detects a defect by comparing the detection image to the average reference image thus generated.

4 Claims, 4 Drawing Sheets

U.S. PATENT DOCUMENTS

| | | |
|---|---|---|
| 5,638,465 A | 6/1997 | Sano et al. |
| 5,943,551 A | 8/1999 | Schemmel et al. |
| 5,966,677 A | 10/1999 | Fiekowsky |
| 6,456,899 B1 | 9/2002 | Gleason et al. |
| 6,512,843 B1* | 1/2003 | Kuwabara .................. 382/149 |
| 6,539,106 B1 | 3/2003 | Gallarda et al. |
| 6,546,120 B1 | 4/2003 | Etoh et al. |
| 6,779,159 B2* | 8/2004 | Yokoyama et al. ............. 716/4 |
| 6,840,666 B2 | 1/2005 | Enachescu et al. |
| 7,149,343 B2 | 12/2006 | Enachescu et al. |
| 7,260,256 B2* | 8/2007 | Hiroi et al. ................. 382/141 |
| 7,346,207 B2* | 3/2008 | Ishikawa ................... 382/145 |
| 7,457,455 B2* | 11/2008 | Matsui et al. ............... 382/149 |
| 2002/0001405 A1 | 1/2002 | Yonezawa |
| 2002/0114506 A1 | 8/2002 | Hiroi et al. |
| 2002/0159101 A1 | 10/2002 | Alderson et al. |
| 2002/0188917 A1* | 12/2002 | Yokoyama et al. ............. 716/4 |
| 2003/0063792 A1 | 4/2003 | Hiroi et al. |
| 2004/0066962 A1 | 4/2004 | Sasa et al. |
| 2005/0117796 A1 | 6/2005 | Matsui et al. |
| 2006/0110009 A1 | 5/2006 | Klassen et al. |
| 2006/0159333 A1* | 7/2006 | Ishikawa ................... 382/149 |
| 2007/0177787 A1 | 8/2007 | Maeda et al. |

FOREIGN PATENT DOCUMENTS

| | | |
|---|---|---|
| JP | 04129241 A | 4/1992 |
| JP | 5-218160 | 8/1993 |
| JP | 09178666 A | 7/1997 |
| JP | 10-74812 | 3/1998 |
| JP | 11-160247 | 6/1999 |
| JP | 2000-97869 | 4/2000 |
| JP | 3091039 U | 10/2002 |

\* cited by examiner

PATTERN DEFECT INSPECTION METHOD AND APPARATUS

RELATED APPLICATION

This application is a Continuation of U.S. application Ser. No. 10/995,512, filed Nov. 24, 2004, now U.S. Pat. No. 7,457,455, claiming priority of Japanese Application No. 2003-398312, filed Nov. 28, 2003, the entire contents of each of which are hereby incorporated by reference.

FIELD OF THE INVENTION

The present invention relates to a method and apparatus for performing defect inspection while detecting the images of a plurality of patterns as formed on or above an object to be tested, such as a semiconductor wafer, photo-mask, printed circuit board or equivalents thereto.

BACKGROUND OF THE INVENTION

Figure 4:
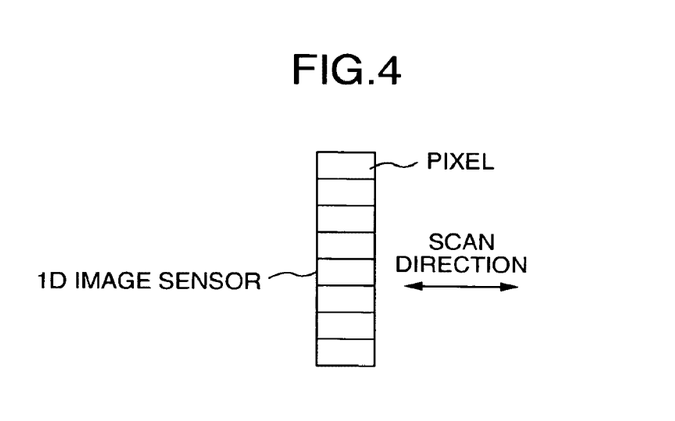
FIG. 4 is a diagram showing the structure of an image sensor.
Figure 5:
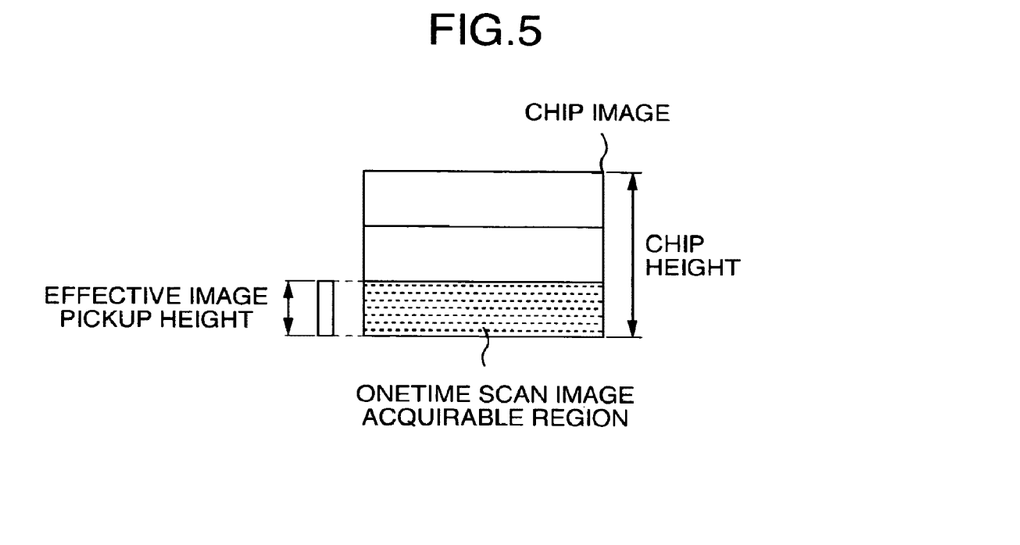
FIG. 5 is a plan view of an inspection area of an object to be tested.

Typically in pattern defect inspection procedures, a one-dimensional (1D) or linear image sensor is used as the image detection means for picking up the image of an object to be tested. FIG. 4 is a diagram showing an arrangement of such image sensor 8, and FIG. 5 is a plan view of an inspection area of the object being tested, for indicating the area that is image-detectable by a single time of scanning. Scan the object under test in a direction at right angles to the layout direction of picture elements or "pixels" 81 of the image sensor 8, thereby acquiring a two-dimensional (2D) image. The length of the direction along which the pixels 81 are queued is called the "height" of the image sensor 8. In addition, in case the object under test is assumed to be a semiconductor wafer having a plurality of semiconductor chips being presently fabricated, the length of a single chip in the same direction as the height of image sensor 8 is called the chip height. Generally the chip height is larger than the height of image sensor 8, so it is merely possible to detect only an image of part of the chip through one-time scanning of the image sensor 8. The significance of this chip's partial image is determinable depending upon the height of the image sensor 8 that performs detection and the imaging magnification of an image focussing optical system for projecting the chip image onto this image sensor 8. This height is called the effective image pickup height of the image sensor 8. In a combination of a currently used image sensor and its associated image focusing optical system, the effective image pickup height is less than the chip height. Accordingly, in order to inspect an overall chip surface, a method is employed for scanning it while offsetting in the height direction for multiple times.

Figure 6:
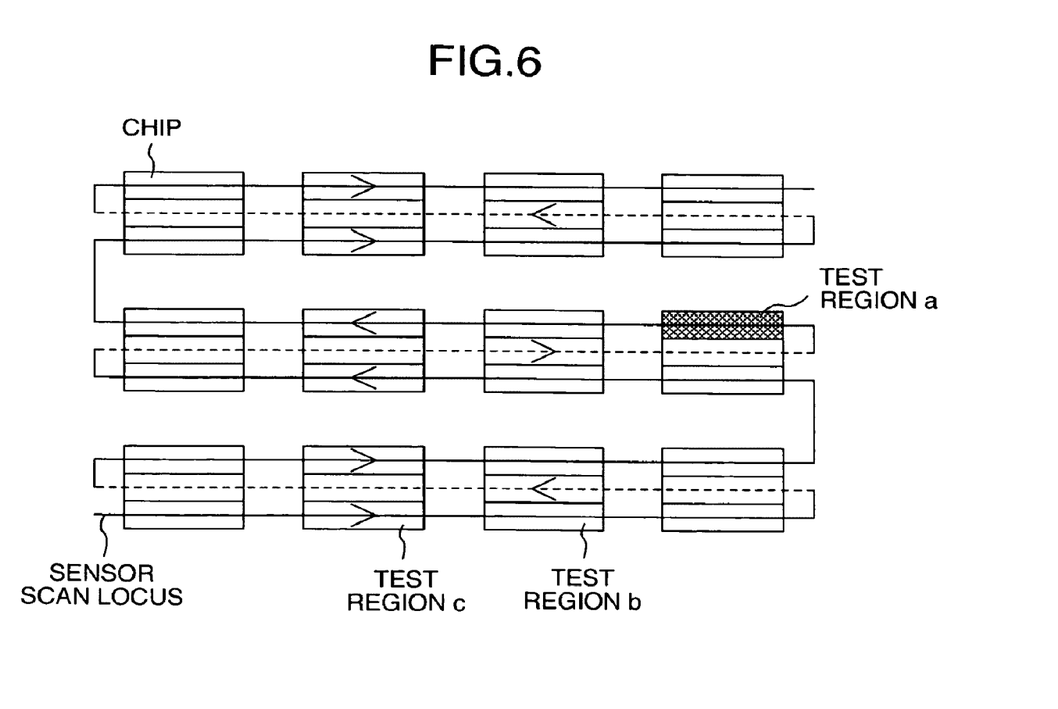
FIG. 6 is a plan view showing a sensor scan locus in case a plurality of chips are scanned by the image sensor for multiple times.

FIG. 6 is a plan view diagram showing a sensor scan locus 101 in case a plurality of chips 21 that are formed on a wafer are scanned by an image sensor for several times. Usually in the pattern defect inspection apparatus, the image sensor is fixed while using a stage to move the wafer under test. Firstly, let the test object move in the X direction; then, acquire an image. Information per pixel of one chip 21 is stored in a memory in the order of scanning. After having completed the image detection in a one-time scan cycle, let the test object move in the Y direction by a distance corresponding to the effective image pickup height of the image sensor. The stage is driven to shift in position as indicated by broken line in FIG. 6 so that the scan direction becomes reversed. This will be repeated to thereby achieve sequential image detection.

While inspection of the chip 21 is performed by image comparison of the same patterns, the image of a test area "c" is used as a reference image in the case of testing an area "b." However, when testing an area "a" that is the forehand chip of each row to be scanned, it is impossible to perform any intended inspection due to the absence of a reference image in an area immediately preceding the same pattern. This would result in generation of noninspectable areas or regions in the outer periphery of the wafer. For this reason, non-inspectable chips would take place in those in the wafer outer periphery.

Figure 7:
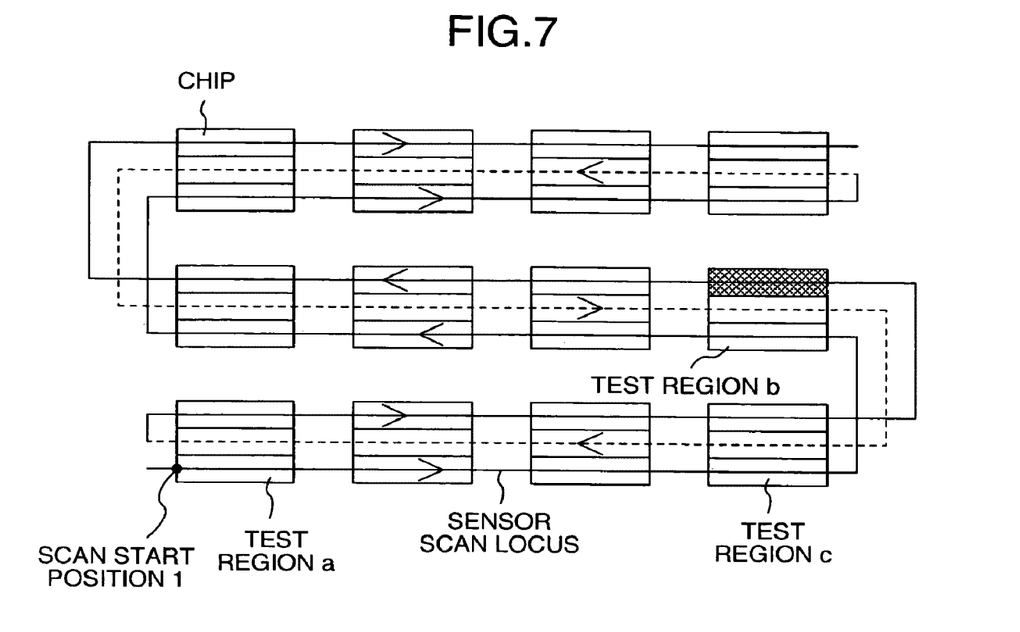
FIG. 7 is a plan view showing an image sensor scan locus.

In prior known pattern defect inspecting apparatus, there is the one that solved the above-noted problem by modifying the scan method (for example, see JP-A-11-160247). FIG. 7 is a plan view showing the scanning locus of an image sensor in a similar way to FIG. 6. In this case, the effective image pickup height of the image sensor is one-third (⅓) of the chip height. Assume that scanning is done while dividing the test area into three strip-like regions. Although the scanning of the first row in the X direction is the same as that shown in FIG. 6, the second row is scanned while causing an object under test to move by a distance corresponding to the height of one chip in the Y direction. This will be repeated for execution of comparative inspection of the images of identical patterns each having its region equal in size to ⅓ of a chip. Upon completion of the last row, as indicated by dotted line in FIG. 6, the image of the same pattern in the next ⅓ regions of the chip is subjected to comparison inspection. After having finished the first chip, comparison inspection is done for the image of the same pattern in the remaining ⅓ region of the chip.

In the case of testing of an area "b" which is immediately after a fold-back or a halfway point, the pixel information of the area "c" for use as a reference image is read out in an order reverse to the order at the time of data storage, whereby the comparison inspection is executable while letting the area b and area c be the same pattern image. Optionally, the image of another area of the same pattern may be prestored as the reference image of the area a upon startup of the inspection. Whereby, it is possible to perform the inspection of the area a also.

However, in any one of the pattern defect inspection apparatus for performing inspection based on the scan locus shown in FIG. 6 and the pattern defect inspection apparatus for performing inspection relying upon the scan locus shown in FIG. 7, comparative inspection of the detection image of a chip is performed by comparing it to the reference image of its immediately preceding chip with the same pattern. Using the image of such immediately preceding chip in this way raises problems which follow.

Figure 1:
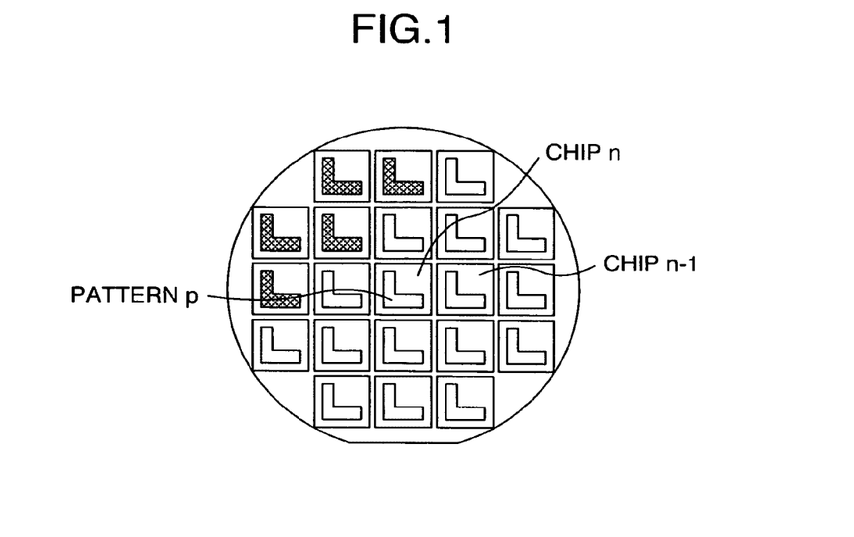
FIG. 1 is a diagram showing a plan view of a wafer having its surface on which a pattern made of a transparent thin film is formed.

An object under test for use as the object being subjected to pattern defect inspection is such that a pattern is typically formed of a material that is transparent with respect to the wavelength of visible light, such as a photo-resist or a dielectric film made of $SiO_2$ or the like. In this case, even if a thin film is transparent relative to the wavelength of light being used in the defect inspection apparatus, it exhibits certain reflectivity which is determinable by such the light wavelength and the refractivity of a material making up the pattern plus a film thickness. This makes it possible for the defect inspection apparatus to detect its presence as a light-and-shade image. FIG. 1 shows an exemplary wafer having a pattern of thin film formed thereon, which is made of a material transparent to the wavelength of light being used in the defect inspection apparatus. Generally in such the wafer, the thickness of the thin film pattern is not perfectly flat on an entire wafer surface but slightly different depending on locations; however, a certain degree of film thickness error is made acceptable because such error does not affect the manufacture of semiconductor chips. Unfortunately, a difference in film thickness occurring depending on locations can create a likewise difference in reflectivity of the pattern, resulting in occurrence of an appreciable difference in brightness or luminance of an image to be detected. This phenomenon is called the color shading irregularity. For example, suppose that a neighboring chip "n" and its immediately preceding chip n−1 of FIG. 1 are such that the same shaped patterns "p" included therein are different in film thickness from each other, resulting in occurrence of color shading. In this case, if the comparison inspection is carried out while letting the chip n be a detection image and also regarding the chip n−1 as a reference image, then the pattern p must be erroneously detected as a defect. This occurs because the resultant image is different in light-and-shape property even though the pattern p is the same in shape between these two images and no defects are present therein. Such the false defect information raises difficulties in distinction from a true defect and thus is a serious problem relating to the reliability of the inspection apparatus.

Prior known approaches to avoiding the above-noted false defect information include two methods which follow:

(1) increasing the threshold value so that the color shading irregularity is insensitive to test results during inspection while comparing a detection image to reference image, wherein the threshold value becomes a criterion for judgment of which degree of difference is regarded as a dominant difference; and (2) correcting or amending the influenceability of color shading irregularity occurring between the detection image and reference image and then performing comparison inspection after removal of the color shading.

The advantage of the method (1) does not come without accompanying the following penalties: the inspection apparatus decreases in detection sensitivity; and, its detection ability or "detectability" for true defects decreases simultaneously. Regarding the method (2), this is a method such as shown in JP-A-2000-97869 for example. Estimation of the degree of the color shading at a chip position of the detection image from the reference image of its immediately preceding chip is equivalent in principle to estimating by interpolation unknown information in the future from known information in the past. In addition, utilizable information items are as less as two images i.e., a single plane of detection image and a reference image plane. Thus, this method is disadvantageously limited in effects for enabling correction and removal of the color shading influenceability.

A pattern inspection apparatus is disclosed in JP-A-10-74812, which apparatus detects an image signal from a repeated pattern to be tested, and generates from this detected image signal a statistical image signal of the repeated pattern being tested, and then uses this generated statistical image signal as a reference image signal to compare it to the above-noted detected image signal while applying thereto position alignment, thereby extracting a defect or a defect candidate that is present in the pattern under test.

JP-A-3-286383 discloses therein a surface defect inspecting apparatus for detecting defects based on a pattern difference. This apparatus comprises means for sequentially accepting first patterns, pattern generator means for calculating an average value of the first patterns accepted by the accepting means to thereby generate a second pattern, and means for comparing the second pattern thus generated to a newly accepted first pattern and for detecting a pattern difference, if any.

JP-A-5-218160 discloses a semiconductor chip appearance inspection apparatus which includes a first image memory that sequentially temporarily stores dark-and-light grayscale information of a plurality of semiconductor chips obtained by dicing a single piece of wafer, a second image memory for storing reference grayscale information used for execution of comparative judgment by comparison with the grayscale information of the first image memory, a defect-free product detector unit for comparing the grayscale information of the first image memory to that of the second image memory to thereby detect non-defective semiconductor chip products, and an image averaging processor unit for performing, when the defect-free product detector unit judges a chip as a good product, computation of the grayscale information of the first and second image memories, for rewriting the grayscale information of the second image memory based on the computation result, and for allowing the rewritten information to become a new reference grayscale information.

SUMMARY OF THE INVENTION

An object of this invention is to provide a pattern defect inspection apparatus capable of improving the accuracy of pattern defect inspection even when a pattern which is formed of a transparent thin film is different in thickness between the position of a detection image and the position of a reference image. Another object of the invention is to provide a pattern defect inspection method with such the capability.

To attain the foregoing objects, the invention employs a technique for generating an average reference image from the images of a plurality of more than two patterns of identical shape—these include forth and back ones lying relatively near to a detection image with at least the detection image being interposed therebetween of those patterns having the same shape as continuously laid out on an object being tested at equal intervals in row and column directions.

To do this, the invention comprises a means for storing therein a detection image and the images of a plurality of more than two identical shape patterns containing the forth and back ones lying next to the detection image with at least the detection image interposed therebetween, an average reference image generator means for generating from such the stored images an average reference image through statistical computation processing, and an image comparator means for performing comparison inspection of the detection image and the average reference image to thereby detect defects, if any.

A feature of the invention lies in creation of the average reference image by statistical computation processing from four identical shape patterns on the up-down and right-left sides of the detection image, with two further patterns in the up-down directions being added thereto.

With this arrangement, it is possible, by generating the reference image from at least four up-down and right-left images with the detection image interposed therebetween, to obtain the intended reference image which approximates the color shading irregularity at the detection image position. Thus it is possible to effectively suppress color shading influenceabilities during comparison testing of this reference image and the detection image. This in turn makes it possible to provide the pattern defect inspection method and apparatus capable of improving the accuracy of pattern defect inspection even for an object under test that is relatively large in color shading influenceability.

According to the invention, it is possible to achieve an improved pattern defect inspection apparatus capable of removing or suppressing the color shading influenceability to thereby detect defects with high inspection accuracy even in cases where a pattern is formed of a transparent thin film on or above the object under test with the transparent thin film being variable in thickness depending upon locations overlying the object under test.

A pattern defect inspection apparatus of the present invention is the one that detects defects by comparing a detection image, which is obtainable by scanning using an image sensor those patterns having the same shape as continuously laid out on an object to be tested at equal intervals in row and column directions, to a reference image obtained by scanning such the identically shaped patterns residing side-by-side in the row and column directions. This apparatus is characterized by comprising means for generating an average reference image through statistical computation processing from the images of identical shape patterns residing next to a detection image, including eight nearest chips that neighbor the detection image on up-down and right-left sides and at oblique or diagonal positions with the detection image interposed therebetween, and means for comparing the detection image to the generated average reference image to thereby detect defects, if any.

In accordance with this arrangement, the reference image is generated from at least the eight, up-down and right-left plus diagonally neighboring nearest images with the detection image intermediately situated. Thus it becomes possible to obtain the reference image that approximates the color shading state at the detection image position so that it is possible to effectively lighten the color shading influenceability during comparison testing of this reference image and the detection image. This makes it possible to provide the intended pattern defect inspection method and apparatus capable of improving the accuracy of pattern defect inspection even for those objects under test with large color shading influenceability.

The statistical computation processing for generating the average reference image includes the step of performing simple averaging of the pattern of the nearest same shapes which reside next to the detection image on its up-down and right-left sides and at diagonally neighboring locations.

Alternatively the statistical computation processing for generating the average reference image includes performing calculation of an adaptable quadratic curved plane from eight nearest identical shape patterns which lie relatively near to the detection image on the up-down and right-left sides and also at diagonally neighboring positions.

A scheme for calculating the adapted quadratic curved plane is a least-squares method. To this end, the apparatus includes a means for calculating a mean square error at the same time during such calculation, means for using the mean square error to determine a threshold value for use during defect detection judgment, and means for judging based on this threshold value the presence or absence of a defect(s).

Optionally the invention is configurable in the form of a pattern defect inspection apparatus for detecting defects by comparing a detection image obtainable through scanning, by an image sensor, patterns having the identical shape and being continuously laid out on an object to be tested at equal intervals in row and column directions with a reference image obtained by scanning neighboring identical shape patterns in the row and column directions thereof, wherein the apparatus comprises means for generating an average reference image by statistical computation processing from both the detection image and the images of identical shape patterns residing next to the detection image including at least eight nearest chips on up-and-down and right-and-left sides and at diagonally neighboring positions with at least the detection image being intermediately situated, and means for detecting a defect by comparing the detection image to the average reference image thus generated.

Other objects, features and advantages of the invention will become apparent from the following description of the embodiments of the invention taken in conjunction with the accompanying drawings.

DETAILED DESCRIPTION OF THE EMBODIMENTS

One embodiment of the invention will be explained with reference to the accompanying drawings.

Figure 8:
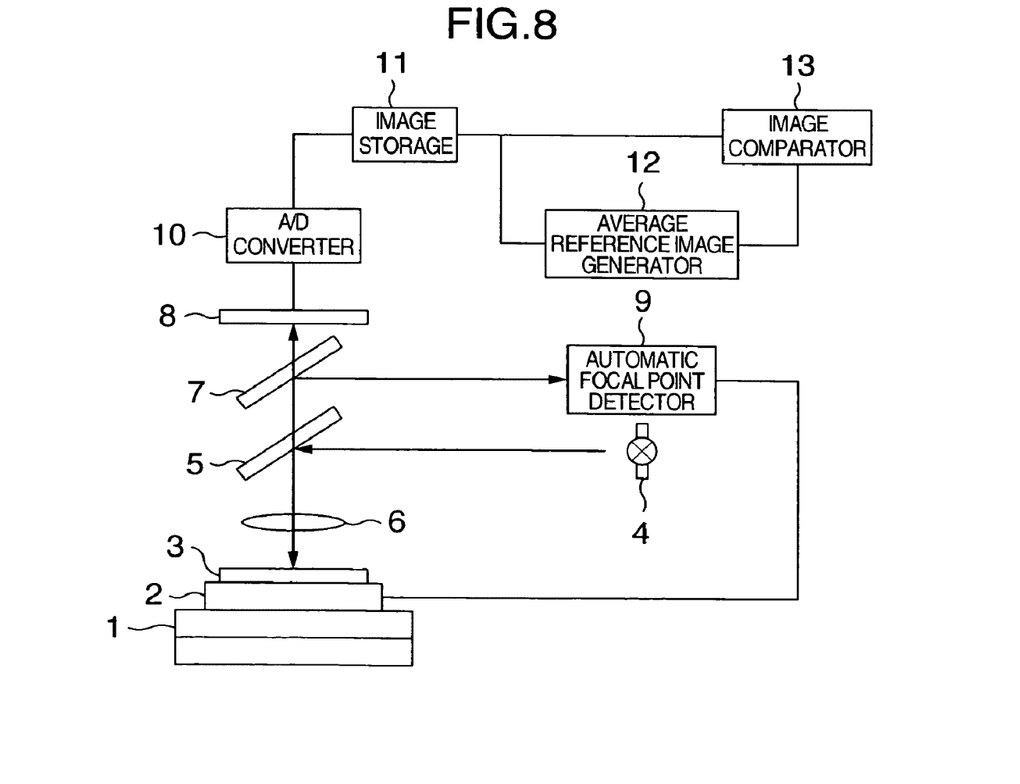
FIG. 8 is a diagram schematically showing a configuration of a pattern defect inspection apparatus.

FIG. 8 is a diagram schematically showing a configuration of pattern defect inspection apparatus. A wafer 3 that is an object to be tested is fixed onto a rotatable Zθ stage 2, which is movable in its height direction. The Zθ state 2 is situated on an X-Y stage 1 that is position-slidable in an X direction that is the horizontal direction and also in Y direction.

A half mirror 5 is located above the wafer 3, for directing illumination light from an illumination light source 4 toward the wafer 3 side to thereby illuminate the wafer 3 via an objective lens 6. Reflection light as given off from a top surface of the wafer 6 is guided to pass through the objective lens 6 and half mirror 5 to reach an image sensor 8, which receives it as detection light. Additionally the light that was split by the half mirror 7 enters an automatic focal point detector means 9, which calculates the optimum focussing position and then gives a movement instruction to a Z state of the Zθ stage 2, thereby enabling detection of an image at the optimum focal point. The detection light received by the image sensor 8 is passed through an analog-to-digital (A/D) converter 10 for conversion into a digital signal, which is then stored or recorded in an image storage means 11.

As the chip height is generally greater than the effective image pickup height of the image sensor 8, a process of testing an overall surface of a chip 21 includes the steps of subdividing an area of chip 21 by the effective image pickup height of the image sensor, and performing a multiplicity of scanning operations while shifting it in the height direction every time scan is done. An example is as follows. Suppose that the effective image pickup height of the image sensor is one-third (⅓) of the chip height. Also assume that the scanning is performed while dividing the test area into three regions. If this is the case, the scanning procedure is as follows: as shown in FIG. 7, after having performed the first-time scanning in the X direction from its left to right, let the object under test move in the Y direction by a distance corresponding to one chip height; then, perform a second scan operation. This will be executed iteratively to thereby perform comparison inspection of an image of the same pattern equivalent to the chip's ⅓ region. Upon completion of the last line, perform comparison inspection of an image of the same pattern of the chip's next ⅓ region as indicated by broken line in FIG. 7. When the first chip is ended, perform comparative inspection of an image of the same pattern of the chip's remaining ⅓ region whereby the inspection of the entire surface area of the chip 21 is completed.

Figure 2:
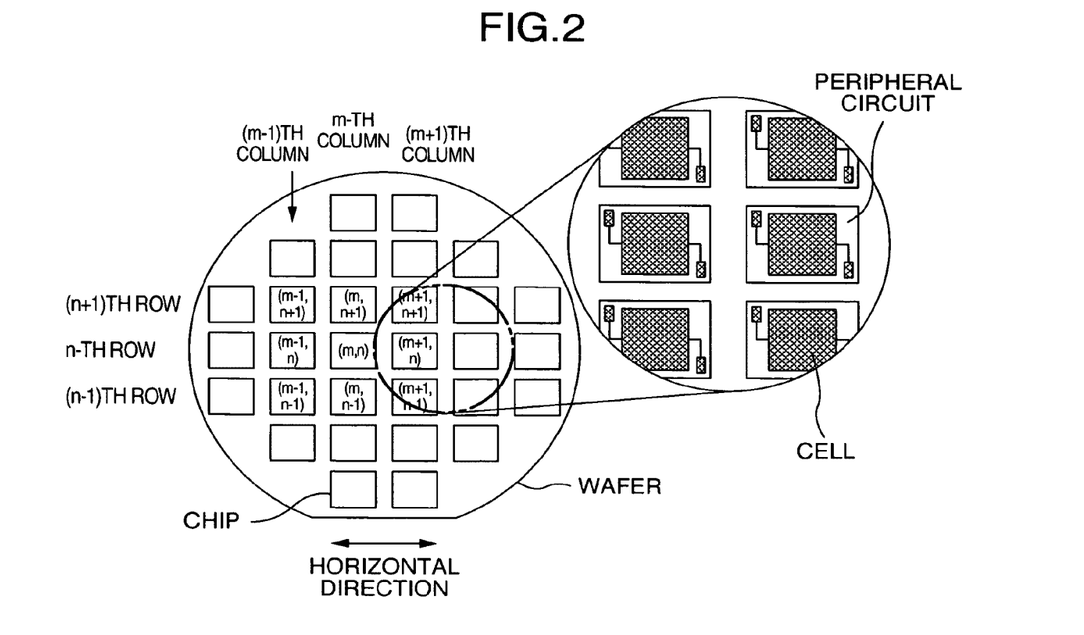
FIG. 2 is a plan view of a semiconductor wafer, along with an enlarged partial view of it.

As will be described later, the embodiment of this invention is arranged so that a reference image which is for use as an object being subjected to comparison inspection with the detection image is created from the images of eight nearest chips lying next to the chip of detection image on its up-down and right-left sides plus at diagonally neighboring positions. To this end, the above-noted image detector means 11 is required to have a capacity capable of storing all images corresponding to the effective image pickup height of the image sensor 8 with respect to a queue of three rows of chips. Note here that the term "right-left" refers to the front and rear or forth and back of the detection image in the scan direction, whereas "up-down" should be interpreted as the upper and lower portions of the detection image when folded back while the scan direction is changed by the chip height. The language "diagonally neighboring" is intended to mean four neighboring images on the "up-down" sides when folded back while changing the scan direction by the chip height. Details are shown in FIG. 2. Assume that the wafer under test is 300 mm in diameter, the pixel size at the time of inspection (size on the object under test) is set at 0.2 μm×0.2 μm, and a total number of pixels in the image sensor height direction is 4,096. Supposing that a 1 byte of memory space is required to store image information per each pixel, the storage capacity required is given as:

300mm÷0.2 μm×4,096×1 byte×3=approx. 17 gigabytes(GB), (where, 1 GB=1,073,741,824 bytes). Traditionally, this large capacity was achievable only by magnetic recording media of extremely low recording speeds, so it has been considered unrealistic to realize such the technology in the pattern defect inspection apparatus that is required to perform processing on a real-time basis during inspection. Fortunately, recent advances in semiconductor device technologies make it possible to attain such degree of storage capacity by use of an ensemble of semiconductor memories.

FIG. 2 is a plan view of a semiconductor wafer along with its enlarged partial view. In the pattern defect inspection apparatus of this embodiment, an image of a region adjacent to the test area is stored for later use as the reference image. This reference image is compared to an image of the test area to thereby extract as a defect a different portion between the both. On the single pierce of wafer 3 shown in FIG. 2, a plurality of chips 21 are laid out, each of which becomes an individual product. These chips 21 are continuously disposed, as patterns of identical shape, at equal intervals in the row and column direction. Here, an explanation will be given of an operation in the case of detecting whether defects are present or absent in a test area "a" within a chip (m, n). Sequentially scan the wafer of an object under test in the order of (n−1)th, n-th and (n+1)th rows. Upon completion of the scanning up to a chip in the (m+1)th column of the (n+1)th row, the resultant image is stored in the image storage means 11. At this time, the average reference image generator means 12 sequentially calculates a simple mean value (arithmetic average) of the signal intensity values of corresponding pixels of eight images of:

(m−1, n−1),
(m, n−1),
(m+1, n−1),
(m−1, n),
(m+1, n),
(m−1, n+1),
(m, n+1), and
(m+1, n+1), thereby to produce an averaged reference image as the average of these eight images. It should be noted that since respective chips of the (n−1)th and (n+1)th rows and each chip of n-th row are such that the stage's scan direction is reversed, read-out is performed in the opposite direction during reading of the stored image(s), thereby attaining equalization of the direction of image information.

Next, an image of chip (m, n) is read out as the detection image, which is passed to the image comparator means 13 together with the above-noted average reference image. This image comparator means sequentially performs comparison of the signal intensity values of pixels corresponding to these two images. Thus, if a pixel is found to have a difference greater than a prespecified threshold value, then such pixel is detected as a defect.

In view of the fact that the average reference image created in this embodiment is calculated from the eight nearest chips on the up-down and right-left sides and at diagonal positions with the chip of the detection image being interposed therebetween, an image at a central chip position is obtained by interpolation from the images of these eight peripheral chips. Due to this, it is expectable that the status of color shading irregularities to be contained in this average reference image is sufficiently proximate to the color shading state at the chip of the detection image residing at the center of these eight chips, except for a special case where the thickness of a transparent thin film making up the pattern rapidly changes to exhibit appreciable increment and decrement with respect to the chip layout interval. Generally, it is assumable that semiconductor wafers are such that the interval or layout pitch of chips is less than or equal to ⅒ of the wafer diameter. Also assume that in those semiconductor wafers with film thickness errors falling into an allowable range, changes in thickness of the pattern-forming transparent thin film exhibit a simple increase or decrease distribution within the chip interval. As apparent from the foregoing, it is possible for the defect inspection method of this embodiment to obtain ultimate efficacy by simplified calculation processing, when compared to the methodology of estimating and correcting the degree of color shading irregularity at the chip position of the detection image by using only the information of a total of two images of the detection image one surface and the reference image one surface of its immediately preceding chip, as has been discussed in the introductory part of the description for example, such as the one indicated for example in JP-A-2000-97869.

Figure 3:
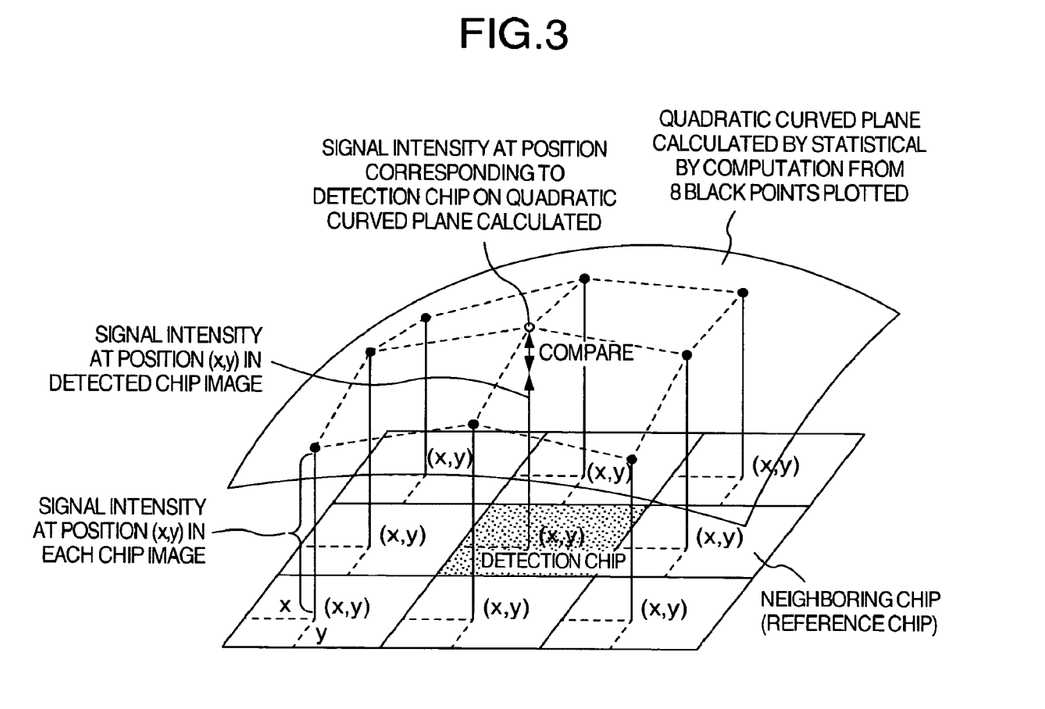
FIG. 3 is a diagram representing a quadratic curved plane thus calculated.

Note here that although in the above embodiment the average reference image is obtained by calculation of the simple mean value (arithmetic average) of the eight nearest chips in the periphery of the detection image on a per-pixel basis, similar results are obtainable by a process having the steps of using a least-squares method to obtain, per each pixel corresponding to one of these eight chip images, the best adaptable quadratic curved plane:

$$g(x,y)=ax^2+by^2+cxy+dx+ey+f,$$ (Eq. 1)

then, identifying the value of g(x, y) at the chip position of a centrally located detection image, and next defining this value as the signal intensity concerning the brightness or luminance of such pixel. More specifically, the statistical computation method for generating the average reference image includes calculating a quadratic curved plane with respect to the signal intensity of the luminance on each corresponding pixel of the eight nearest chip images, obtaining the signal intensity on the quadratic curved plane corresponding to a pixel at the g(x, y) point of the detection image, and then comparing this averaged signal intensity to a signal at the above-noted g(x, y) point. FIG. 3 shows an example of such quadratic curved plane. Black dots as plotted herein represent the signal intensities at positions (x, y) within respective chip images. Eight points of black dots are used to calculate the quadratic curved plane by statistical computation, thereby obtaining the signal intensity at a position corresponding to detection on the quadratic curved plane thus calculated relative to the signal intensity at a position (x, y) within a detection chip image as indicated by a star sign or asterisk. Although an explanation as to its intermediate calculation process is eliminated herein, this calculation resultingly becomes very simple. The signal value of each pixel of the average reference image may be calculated as:

$$I_{m,n} = -0.25 \times I_{m-1,n+1} + 0.5 \times I_{m,n+1} - 0.25 \times I_{m+1,n+1} + 0.5 \times I_{m-1,n} + 0.5 \times I_{m+1,n} - 0.25 \times I_{m-1,n-1} + 0.5 \times I_{m,n-1} - 0.25 \times I_{m+1,n-1}$$

where, "Ip, q" denotes the signal value of the pixel of interest at a chip (p, q). With this method, the calculation procedure becomes somewhat complex when compared to the simple mean value (arithmetic average); however, it offers an advantage as to an ability to generate the average reference image with enhanced accuracy even in cases where the film thickness rapidly changes with respect to the chip interval.

Additionally in light of the fact that in this method using the least-squares method, it is possible to simultaneously obtain the mean square error (i.e., an expectation value of a square error between the quadratic curved plane thus obtained and the original sample data), there is another advantage. Typically even when comparing identical shape patterns having no defects, calculation of an image difference does not always result in zero due to the presence of various kinds of noise components attempting to superposing image signals and/or fluctuation or else of micro-shapes that are too small to be categorized as defects. For this reason, when judging whether defects are present or absent, a need is felt to detect as defects only in case the image difference exceeds a fixed value that was preset as a threshold value. Unfortunately, determining the threshold value is such that appropriate setup accompanies difficulties which follow: if it is too large, then the resultant sensitivity decreases unnecessarily; alternatively, if too small then noise components or the like are picked up even where no defects are present in reality, resulting in unwanted production of false defect information. This mean square error acts as a parameter or index indicative of the exact degree of deviation owned by the identical shape patterns contained in these eight chips even after correction of the color shading influenceability using this quadratic curved plane. Accordingly, when using this value to dynamically determine, during testing, the threshold value upon judgment of whether defects are present or absent, it is possible to determine the threshold value while allowing it to reflect the actual variations. It is also possible to perform inspection while automatically increasing the threshold value at certain locations large in noise components and pattern shape fluctuations and adversely automatically lowering the threshold value at those locations less in such influenceability. Thus it becomes possible to obtain an advantage as to the capability for effectively detecting defects.

It should be further understood by those skilled in the art that although the foregoing description has been made on embodiments of the invention, the invention is not limited thereto and various changes and modifications may be made without departing from the spirit of the invention and the scope of the appended claims.

The invention claimed is:

1. A pattern defect inspection apparatus for detecting defects by comparing a detection image obtained by an image sensor, patterns having an identical shape and being continuously laid out on an object to be tested at equal intervals in row and column directions, with a reference image obtained by scanning patterns of the identical shape neighboring in the row and column directions thereof, said apparatus comprising:
 a statistical computation unit which calculates a quadratic curved plane which is adaptable to two-dimensional distribution of signal intensity on each of image pixels of identical shape patterns lying next to the detection image including a predetermined number of nearest chips on up-and-down and right-and-left sides with the detection image being intermediately situated according to the signal intensity on image pixels; and
 a unit which detects a defect by comparing a signal intensity of an image pixel at first a (x,y)-coordinate of the detection image with a signal intensity at second a (x,y)-coordinate of said quadratic curved plane corresponding to said first (x,y)-coordinate.

2. The pattern defect inspection apparatus according to claim 1, wherein the predetermined number of nearest chips is four.

3. The pattern defect inspection apparatus according to claim 1, wherein the predetermined number of nearest chips is eight.

4. A pattern defect inspection apparatus comprising:
 a first stage which fixes a wafer;
 a second stage which situates said first stage;
 an illumination light source which generates first light;
 an optical element which conducts said first light to said wafer;
 an image sensor which detects second light form said wafer, and obtains an image;
 an optical element which conducts said second light to said image sensor;
 a statistical computation unit which uses said image and images surrounding said image, and calculates a quadratic curved plane which is adaptable to two-dimensional distribution of signal intensities of each image pixel of said image and images surrounding said image; and
 a unit which detects a defect by comparing signal intensity of an image pixel at first a (x,y)-coordinate of said image with a signal intensity at second a (x,y)-coordinate of said quadratic curved plane corresponding to said first (x,y)-coordinate.

* * * * *